United States Patent
Bates et al.

(10) Patent No.: US 10,105,159 B2
(45) Date of Patent: Oct. 23, 2018

(54) RECANALIZATION DEVICE

(71) Applicant: W. L. Gore & Associates, Inc., Newark, DE (US)

(72) Inventors: Mark C. Bates, Encinitas, CA (US); Edward H. Cully, Flagstaff, AZ (US); David M. Williams, Flagstaff, AZ (US)

(73) Assignee: W.L. Gore Associates, Inc, Newark, DE (US)

( * ) Notice: Subject to any disclaimer, the term of this patent is extended or adjusted under 35 U.S.C. 154(b) by 404 days.

(21) Appl. No.: 14/198,962

(22) Filed: Mar. 6, 2014

(65) Prior Publication Data

US 2014/0276921 A1    Sep. 18, 2014

Related U.S. Application Data

(60) Provisional application No. 61/794,425, filed on Mar. 15, 2013.

(51) Int. Cl.
*A61B 17/3207* (2006.01)
*A61B 17/221* (2006.01)
*A61B 17/22* (2006.01)
*A61B 17/30* (2006.01)

(52) U.S. Cl.
CPC ...... *A61B 17/32075* (2013.01); *A61B 17/221* (2013.01); *A61B 2017/2217* (2013.01); *A61B 2017/22044* (2013.01); *A61B 2017/22094* (2013.01); *A61B 2017/306* (2013.01)

(58) Field of Classification Search
CPC .... A61B 17/32075; A61B 2017/22094; A61B 2017/2217; A61B 17/221; A61B 17/1214–17/12154; A61B 2017/320766; A61M 25/003; A61M 25/0054; A61M 25/0023–2025/004

USPC .......................................................... 606/159
See application file for complete search history.

(56) References Cited

U.S. PATENT DOCUMENTS

| | | | | |
|---|---|---|---|---|
| 4,745,919 A | * | 5/1988 | Bundy | A61B 17/3207 600/564 |
| 5,135,531 A | * | 8/1992 | Shiber | A61B 8/12 606/159 |
| 5,423,774 A | * | 6/1995 | Fischell | A61M 25/005 604/508 |
| 5,534,024 A | * | 7/1996 | Rogers | A61F 2/07 606/195 |
| 5,843,103 A | * | 12/1998 | Wulfman | A61B 17/320758 606/159 |
| 6,402,771 B1 | * | 6/2002 | Palmer | A61B 17/221 606/114 |

(Continued)

FOREIGN PATENT DOCUMENTS

AT    195 566    2/1958
WO    2011/119872    9/2011

OTHER PUBLICATIONS

International Search Report for PCT/US2014/021550 dated May 28, 2014, corresponding to U.S. Appl. No. 14/198,962, 7 pages.

(Continued)

*Primary Examiner* — Ryan J Severson
*Assistant Examiner* — Charles Wei (57) ABSTRACT

Catheters for the removal of occlusions in a patient's vasculature. Exemplary catheters use a flexible distal end tube which is capable of coiling irregularly within the occlusion and securing it for removal.

19 Claims, 11 Drawing Sheets

(56) References Cited

U.S. PATENT DOCUMENTS

| | | | |
|---|---|---|---|
| 7,104,966 B2* | 9/2006 | Shiber | A61B 17/3207 600/585 |
| 7,172,589 B2* | 2/2007 | Lafontaine | A61B 18/02 606/20 |
| 7,879,067 B2 | 2/2011 | Galdonik et al. | |
| 7,955,344 B2 | 6/2011 | Finitsis | |
| 7,955,345 B2 | 6/2011 | Kucharczyk et al. | |
| 8,409,237 B2 | 4/2013 | Galdonik et al. | |
| 8,603,122 B2 | 12/2013 | Pokorney et al. | |
| 8,608,754 B2 | 12/2013 | Wensel et al. | |
| 8,747,428 B2* | 6/2014 | Fischell | A61M 29/00 606/108 |
| 2003/0040762 A1* | 2/2003 | Dorros | A61B 17/12045 606/159 |
| 2008/0091223 A1 | 4/2008 | Pokorney et al. | |
| 2008/0177277 A1 | 7/2008 | Huang et al. | |
| 2008/0228171 A1 | 9/2008 | Kugler et al. | |
| 2009/0043372 A1* | 2/2009 | Northrop | A61M 25/0013 623/1.15 |
| 2009/0163851 A1 | 6/2009 | Holloway et al. | |
| 2009/0209987 A1* | 8/2009 | Mathews | A61B 17/221 606/159 |
| 2010/0249825 A1* | 9/2010 | Nihalani | A61B 17/12099 606/198 |
| 2011/0230908 A1 | 9/2011 | Finitsis | |
| 2011/0230909 A1 | 9/2011 | Kucharczyk et al. | |

OTHER PUBLICATIONS

NexGen Medical Systems, Inc. XCOIL Thrombectomy Products: XCOIL Thrombectomy Product Line, May 5, 2012. <http://nexgenmedsystem.com/our-products/>.

* cited by examiner

RECANALIZATION DEVICE

FIELD OF INVENTION

The invention relates generally to recanalization devices, and more specifically, to a device for removing a thrombus, foreign body, or other obstruction from a patient's vasculature, particularly a patient's cerebral or peripheral vasculature.

BACKGROUND OF THE INVENTION

Diagnostic and therapeutic medical procedures often require the use of a surgical device to evaluate and/or treat internal regions of the body. A common surgical instrument used for such purposes is a catheter, which is typically inserted through an incision or fenestration within the patient's vasculature, or orifice of the patient's body. For example, a catheter may be used to facilitate imaging or treatment of a patient's vasculature, such as, for example, removal of a thrombus or other obstruction or foreign body. However, many catheters are unfit for use in such circumstances because of the extremely delicate nature of some vasculature, particularly neurovasculature.

Typical catheters utilize techniques such as hydraulic removal of a thrombus, rotating cutting blades for calcified plaque, inflatable means for crushing or dragging a thrombus, or a multiplicity of metal structures that either self-expand or can be expanded to dredge a vessel or remove a stone. One catheter design comprises a preshaped distal end portion designed to facilitate removal of an occlusion from the tortuous vasculature, including neurovasculature. During insertion of the catheter, a sheath straightens and provides column strength to the preshaped distal end portion. Once the catheter is at the occlusion, the sheath is removed so the distal end portion of the catheter can return to its preformed shape to facilitate engagement with and removal of the occlusion from the desired coronary artery.

Many catheters of the prior art fail to address a major concern for applications into the neurovasculature; namely, minimizing the crossing profile (i.e., the cross-sectional area) of the devices. In general, these prior art catheters are assembled devices consisting of many components that need to either be welded in place, or otherwise fixedly attached, for example, using collars or other means of assembly, thus resulting in larger crossing profiles.

Some catheters address the issue of crossing profile by using fixed wire assemblies which are not meant to pass through a microcatheter, but rather, to navigate from a large guiding catheter situated well proximal of the obstruction in large vasculature. For example, some devices use an assembly in which the wire ends are managed into a collar. A retractable core wire doubles as a conventional distal tip. This tip allows the device to navigate the vasculature and puncture a thrombus, while the large body of the device encompasses the expander. However, this design does not address the majority of anticipated cerebral vascular cases, in which microcatheter/guidewire combinations are used to create a pathway across the clot for angiographic visualization distal to the clot prior to the procedure.

Another type of catheter anticipates the need for smaller devices to achieve neurovasculature compatibility. Such devices use a helically shaped wire held straight for delivery by the microcatheter. The use of a single wire shaped into a 'cork-screw' reduces the profile by eliminating complex assembly steps required by earlier catheters. Typically, it is preferred that microcatheters be flexible at the distal end, which makes it difficult for such devices to hold a preshaped wire in a straight configuration. To increase distal end flexibility, such devices utilize a less rigid 'cork-screw,' which degrades its ability to extract a clot. These devices are also limited in their ability to prevent the distal migration of particulate during the removal of clot due to the inherently large interstices of the single, helically shaped 'cork-screw' wire. These devices also require complete removal from the patient following each pass. This adds considerable procedural time and increases radiation exposure to both the patient and the clinical staff.

Thus there exists a need for a recanalization device suited for effective and efficient removal of thrombi from human neurovasculature and peripheral vasculature. Exemplary embodiments of the present invention feature a flexible distal end tube which is capable of more effectively securing thrombus particulate during removal. Those skilled in the art will recognize numerous advantages of such exemplary embodiments over the prior art, for example, reducing distal migration of thrombus particulate during removal.

SUMMARY OF THE INVENTION

The present invention relates to improved recanalization devices which are atraumatic and useful in the removal of thrombi from vasculature, including both peripheral and neurovascular veins and arteries. An exemplary embodiment features a recanalization device which is flexible and reduces distal migration of thrombus particulates during removal of thrombi. These devices are not size limited and may be made in a range of sizes, being useful for embolectomy procedures as well as peripheral and neurovascular procedures.

An exemplary embodiment of the present invention comprises a tip, a polymeric flexible distal end tube comprising a substantially linear state and an irregularly coiled state, and may include an inner mandrel and an actuating mechanism.

Another exemplary embodiment of the present invention comprises a thrombus piercing tip, a flexible distal end tube comprising a substantially linear state and an irregularly coiled state wherein the flexible distal end tube comprises an irregularly corrugated polymer such as porous expanded polytetrafluoroethylene (ePTFE), an inner mandrel which provides structural support for the flexible distal end tube, and a guide wire.

An exemplary method of the present invention comprises introducing a catheter into a patient's body, the catheter comprising a tip, a polymeric flexible distal end tube comprising a substantially linear state and an irregularly coiled state, an inner mandrel, and an actuating mechanism, piercing the occlusion with the tip of the catheter, withdrawing the inner mandrel from the polymeric flexible distal end tube, applying tension to the actuating mechanism, which converts the polymeric flexible distal end tube from the substantially linear state to the irregularly coiled state, and withdrawing the catheter and occlusion from the patient's body.

DETAILED DESCRIPTION OF THE INVENTION

The detailed description of various embodiments herein makes reference to the accompanying drawing figures, which show various embodiments and implementations thereof by way of illustration and best mode, and not of limitation. While these embodiments are described in sufficient detail to enable those skilled in the art to practice the embodiments, it should be understood that other embodiments may be realized and that mechanical and other changes may be made without departing from the spirit and scope of the present disclosure. Furthermore, any reference to singular includes plural embodiments, and any reference to more than one component may include a singular embodiment. Moreover, recitation of multiple embodiments having stated features is not intended to exclude other embodiments having additional features or other embodiments incorporating different combinations of the stated features.

An exemplary catheter of the present invention comprises a flexible distal end tube which can be converted from a first configuration to a thrombus engaging configuration. In exemplary embodiments, the first configuration may be substantially straight, linear, curved, or have any other configuration suitable for navigation of the catheter through the tortuous vasculature. The thrombus engaging configuration on the other hand is suitable for engaging a thrombus in such a way as to facilitate removal of the thrombus. For example, the distal end tube may convert to an irregularly coiled configuration. To achieve such an irregularly coiled configuration, exemplary flexible distal end tubes may comprise various randomness-enhancing structural biases, such as, for example, an eccentric inner and outer surface configuration, regions of varying flexibility, and/or regions of corrugation, as discussed in greater detail below.

In addition to the thrombus engaging configuration of the flexible distal end tube, the tube may also feature different surface characteristics which improve the catheter's ability to engage a thrombus and facilitate its removal from the patent's body. For example, interstices may be formed in the flexible distal end tube to facilitate engaging a thrombus. In various exemplary embodiments, corrugations may improve the ability of the catheter to engage and retain a thrombus. In exemplary embodiments, such as a catheter using an eccentric tube configuration and/or a tube with regions of varying flexibility, interstices or corrugations may form on the surface of the flexible distal end tube when it is converted to the thrombus engaging configuration (e.g., as wrinkles or depressions in portions of the flexible distal end tube). In general, any surface treatment designed to increase the surface area may be used in connection with the present invention.

The present disclosure relates a number of non-limiting, exemplary embodiments, each of which may be used alone or in coordination with one another. For example, corrugations may be combined with a catheter comprising an eccentric flexible distal end tube and/or a flexible distal end tube with regions of varying flexibility.

Figure 1A:
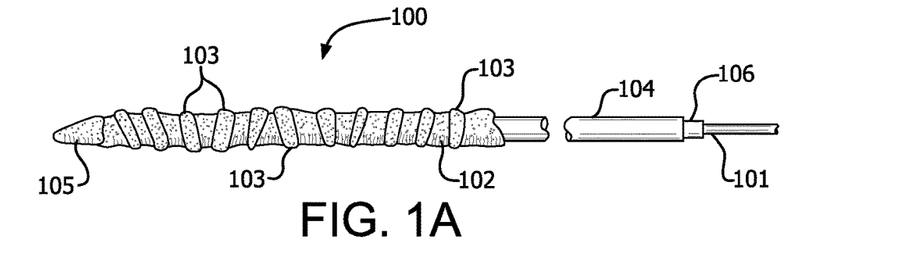
FIGS. 1A-1D illustrate, respectively, an exemplary catheter in a substantially linear configuration, two longitudinal cross-sectional side views of an exemplary catheter and an exemplary catheter in an irregularly (randomly) coiled configuration.
Figure 1B:
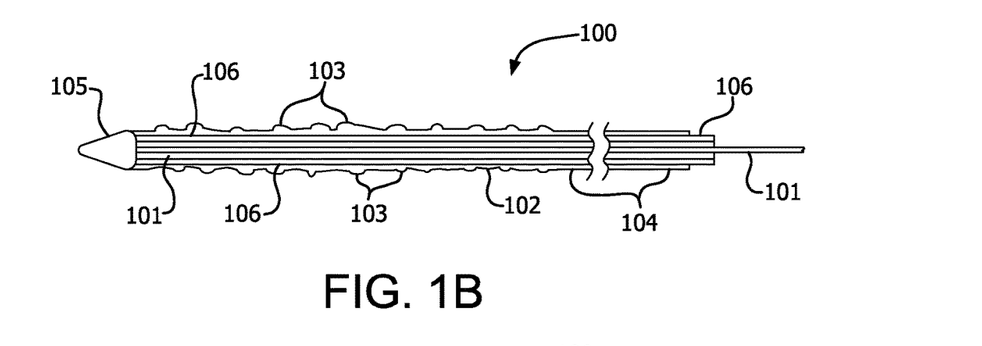

Turning now to such exemplary embodiments, and with initial reference to the side view of FIG. 1A and the longitudinal section of FIG. 1B, an exemplary embodiment is illustrated as catheter 100. Catheter 100 includes a tubular catheter shaft 104, flexible distal end tube 102, stiffening mandrel 106, a tensile actuating mechanism such as wire 101 and distal tip 105. In this illustration, catheter 100 is in a substantially straight configuration. In the substantially straight configuration, flexible distal end tube 102 is given column strength and otherwise supported by the presence of stiffening mandrel 106. In addition, the actuating mechanism 101 is not engaged (i.e., is not under tension) in the substantially straight configuration.

Exemplary flexible distal end tube 102 may further comprise corrugations 103. In various embodiments, flexible distal end tube 102 is corrugated such that corrugations 103 are irregularly shaped and spaced to create a random pattern. A different, random pattern will typically result with each time the catheter is actuated following straightening after a previous actuation. The random pattern will partly be defined by the shape and size of the adjacent anatomy and the shape, morphology and size of the lesion. It is apparent that these random patterns enhance the effectiveness of the catheter and that the physical characteristics of the catheter work with the shape of the anatomy to result in the random patterns. For example, the arrangement of corrugations 103 in flexible distal end tube 102 may vary laterally along the tube. In an exemplary embodiment, a profile (e.g., a longitudinal cross-sectional view) of flexible distal end tube 102 taken at a particular lateral location may comprise a corrugation arrangement that is different from a profile taken at a different lateral location on tube 102.

Figure 1C:
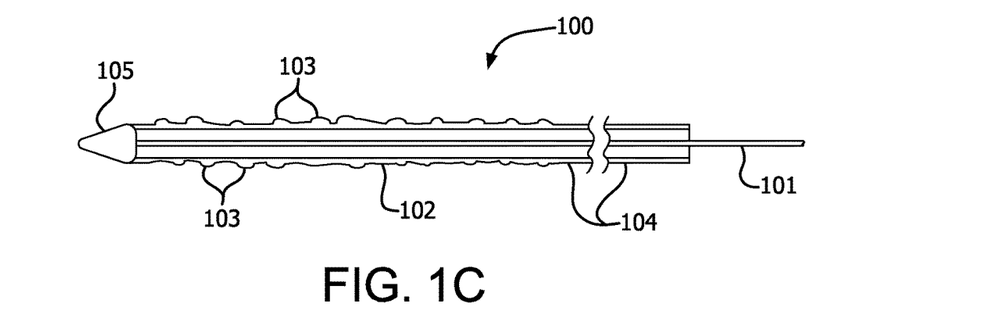

FIG. 1C illustrates a cross-sectional view of the embodiment illustrated in FIG. 1B with exemplary catheter 100 is in a substantially straight configuration. In this configuration, inner mandrel 106 has been removed preparatory to the application of tension to wire 101 and actuation of the flexible distal end tube 102.

Figure 1D:
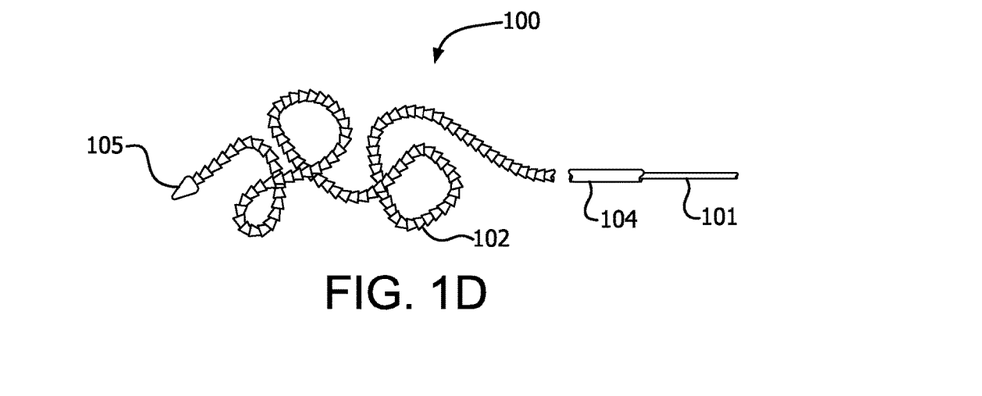

FIG. 1D illustrates an exemplary catheter 100 in an irregularly coiled, random configuration. In this configuration, inner mandrel 104 has been withdrawn from flexible distal end tube 102 as shown in FIG. 1C. Once inner mandrel 104 is withdrawn, the actuating mechanism 101 is engaged by the application of tension to mechanism 101 while holding catheter shaft 104 stationary. As the actuating mechanism 101 is engaged, the distal and proximal ends of flexible distal end tube 102 are drawn closer together, and the tube 102 may change shape randomly as shown in FIG. 1D, influenced by the configuration of corrugations 103. For example, in a preferred embodiment, corrugations 103 are irregularly configured to assist in creating an irregularly coiled shape in flexible distal end tube 102. In exemplary embodiments, the actuating mechanism 104 is a tension filament that is attached directly to the distal end 105 of flexible distal end tube 102. Although the embodiment illustrated in FIGS. 1A-1D features a flexible distal end tube that is entirely corrugated, any arrangement of corrugations or other asymmetrical means that causes the flexible distal end tube to convert to a thrombus engaging configuration is within the scope of the present disclosure.

Figure 2A:
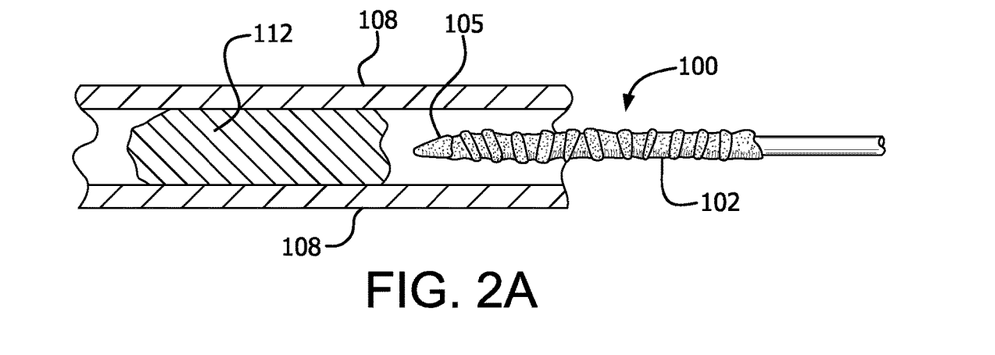
FIGS. 2A, 2B and 2C illustrate side views of an exemplary catheter approaching, penetrating and removing a thrombus.
Figure 2B:
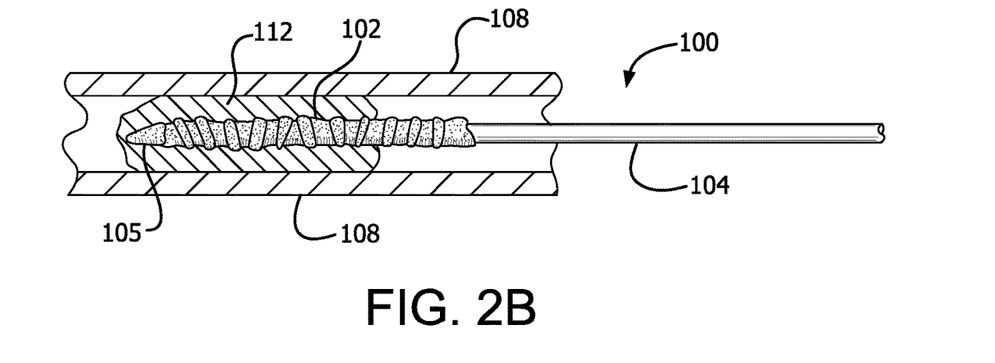
Figure 2C:
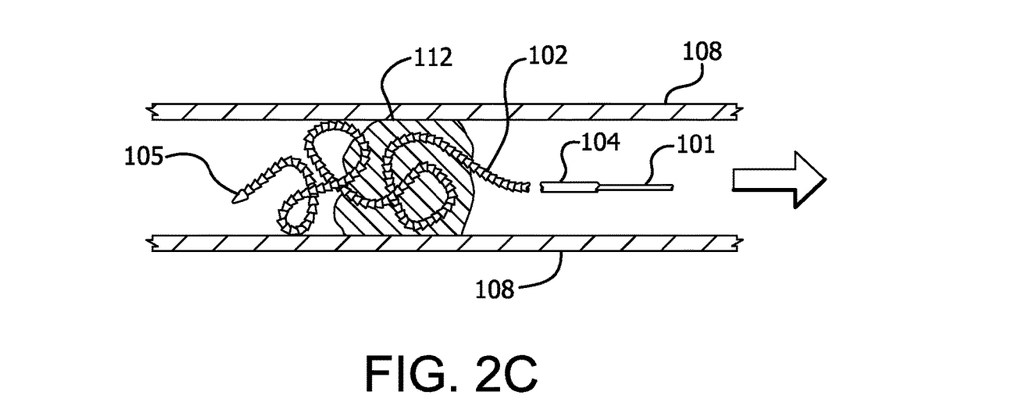

FIGS. 2A, 2B and 2C illustrate side views of an exemplary catheter approaching, penetrating and removing a thrombus 112 located in a vessel 108.

Figure 2D:
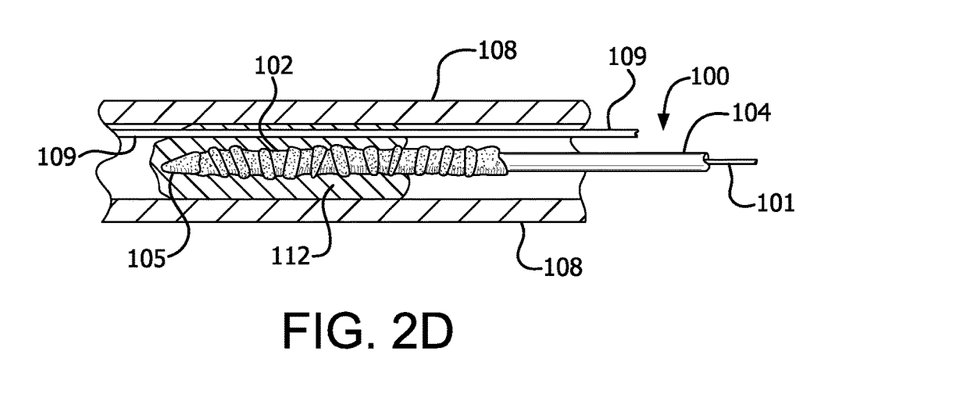
FIG. 2D shows a side view analogous to that of FIG. 2B wherein a separate guidewire is penetrated through the thrombus adjacent to the exemplary catheter.
Figure 2E:
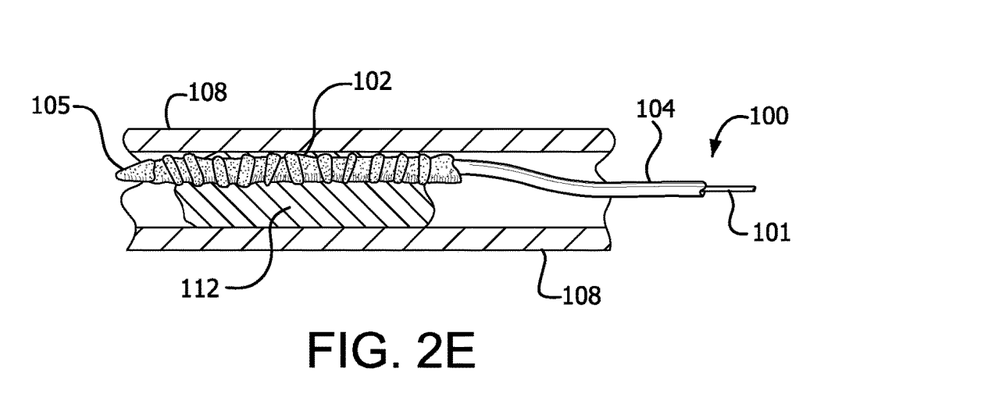
FIGS. 2E and 2F show side views of an exemplary catheter inserted between the thrombus and a vessel wall for removing the thrombus.
Figure 2F:
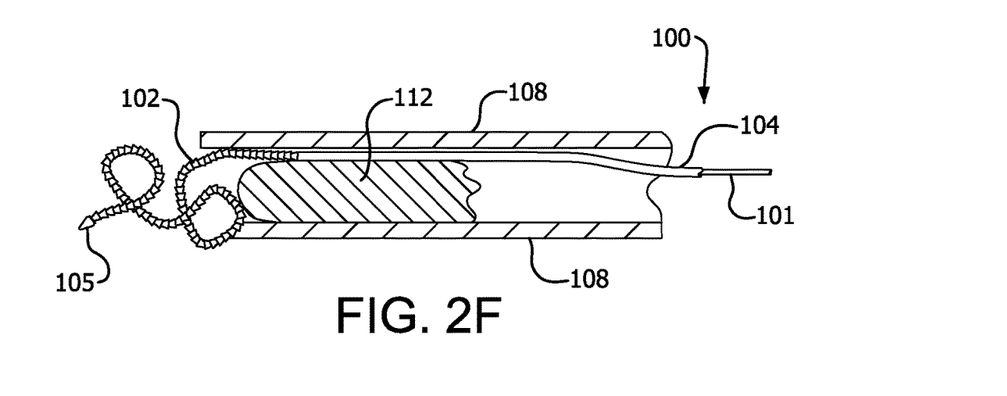

FIG. 2D shows a side view analogous to that of FIG. 2B wherein a separate guidewire 109 is penetrated through the thrombus adjacent to the exemplary catheter. FIGS. 2E and 2F show side views of an exemplary catheter inserted between the thrombus and a vessel wall for removing the thrombus.

Corrugations 103 may be irregularly spaced and shaped to create a random pattern of corrugations. In various exemplary embodiments, corrugations 103 may comprise less than 100% of the surface area of the flexible distal end tube, though in some embodiments, the entire surface may be corrugated.

In various exemplary embodiments, flexible distal end tube 102 comprises a polymer. Exemplary polymers may comprise one or more of nylons, polycarbonates, polyethylenes, polypropylenes, polytetrafluoroethylenes, polyvinyl chlorides, polyurethanes, polysiloxanes, and other biocompatible materials. In a preferred embodiment, flexible distal end tube 102 comprises ePTFE. In various exemplary embodiments, flexible distal end tube 102 is non-metallic.

In various exemplary embodiments, flexible distal end tube 102 may comprise a porous material. For example, flexible distal end tube 102 may comprise a polymer with micro pores. In a preferred embodiment, flexible distal end tube 102 comprises ePTFE wherein the surface of the tube includes micro pores. The presence of micro pores in flexible distal end tube 102 may permit diffusion or the application of a vacuum or suction, allowing for improved thrombus securing and removal capabilities. In various exemplary embodiments, micro pores may allow for drug delivery to the vicinity of the thrombus and/or the use of contrasting agents to facilitate imaging of the vasculature and/or thrombus.

Inner mandrel 106 is generally a tubular element. The term "tubular element" includes any longitudinally extending structure with or without a lumen therethrough. Thus, tubular elements include but are not limited to tubes with lumens, solid rods, hollow or solid wires (e.g., guidewires), hollow or solid stylets, metal tubes (e.g., hypotubes), polymer tubes, pull cords or tethers, fibers, filaments, electrical conductors, radiopaque elements, radioactive elements and radiographic elements. Tubular elements can be of any material and can have any cross-sectional shape including but not limited to profiles that are circular, oval, triangular, square, polygon shaped or randomly shaped.

In a preferred embodiment, inner mandrel 106 is hollow to permit the application of a vacuum or suction, allowing for improved thrombus securing and removal capabilities. Another benefit of a hollow inner mandrel 106 is the ability to deliver drugs or contrast agents or other endoscopy tools.

In various exemplary embodiments, distal tip 105 comprises a tip capable of piercing a thrombus. In various exemplary embodiments, distal tip 105 may comprise a material that is radiopaque. Distal tip 105 may comprise an independent structure. In other exemplary embodiments, distal tip 105 comprises an integrated, densified portion of the end of flexible distal end tube 102 or is otherwise integral and continuous with, and comprised of the same material as, the end of flexible distal end tube 102.

In various exemplary embodiments, the actuating mechanism may comprise a tension filament. The position and configuration of the actuating mechanism may vary in different embodiments. For example, in various exemplary embodiments, the actuating mechanism may comprise a tension filament that is embedded in flexible distal end tube 102. In another embodiment, the tension filament may "weave" in and out of the surface of flexible distal end tube 102. In exemplary embodiments, the tension filament is collinear with flexible distal end tube 102, while in other embodiments, it is not, so as to bias flexible distal end tube 102 toward a random, thrombus engaging configuration during actuation. In various exemplary embodiments, the actuating mechanism may comprise a material that is radiopaque. However, any configuration of the actuating mechanism that allows tension to be applied to flexible distal end tube is within the scope of the present invention.

In general, any structural design or mechanism that randomly compresses and/or changes the shape of flexible distal end tube 102 may be suitable for use as an actuating mechanism in connection with the present invention. For example, heat may be used to randomly compress and/or change the shape of flexible distal end tube 102. In another embodiment, flexible distal end tube 102 comprises a shape memory material having a first random thrombus engaging configuration and a second low-profile insertion configuration, wherein the inner mandrel 104 maintains flexible distal end tube 102 in the second configuration until it is removed. Suction, or negative pressure applied to the lumen of the flexible distal end tube 102 may also provide the necessary force required to actuate. Suction, used in conjunction with a porous distal end tube construct, will also create beneficial high clot retention forces. Importantly, in exemplary embodiments, a sheath need not be removed from flexible distal end tube 102 for it to take on its thrombus engaging configuration.

Figure 3A:
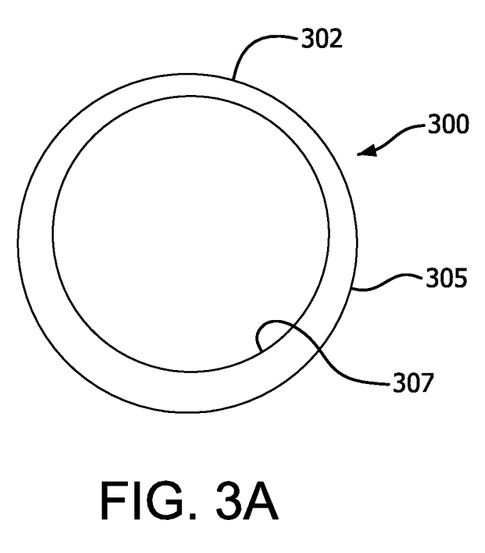
FIGS. 3A and 3B illustrate transverse cross-sectional views of an exemplary catheter.
Figure 3B:
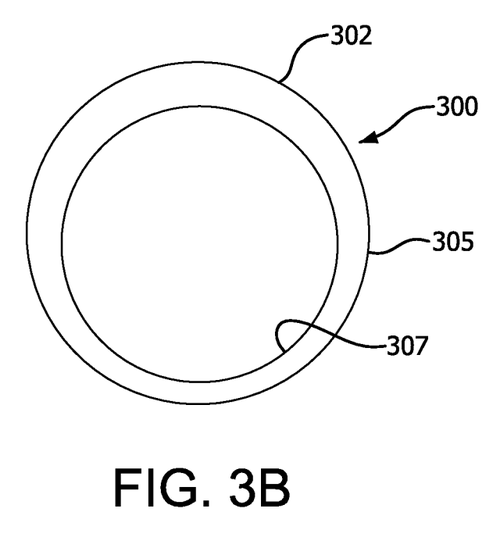

With reference to FIGS. 3A and 3B, two cross-sectional views of an exemplary catheter 300 are illustrated. Catheter 300 includes a flexible distal end tube 302, with an inner surface 307 and an outer surface 305. In such exemplary embodiments, inner surface 307 and outer surface 305 may be considered as eccentric to each other. In various exemplary embodiments, the arrangement inner surface 307 and outer surface 305 in flexible distal end tube 302 may vary laterally along the tube. In various exemplary embodiments, a profile (e.g., cross-sectional view) of flexible distal end tube 302 taken at a particular lateral point may comprise an arrangement of inner surface 307 and outer surface 305 that is different from a profile taken at a different lateral point in the tube, as is demonstrated by FIGS. 3A and 3B.

In exemplary embodiments, such an eccentric arrangement may be useful in biasing random actuation of the flexible distal end tube. In one particular embodiment, as the inner mandrel is withdrawn from the flexible distal end tube, the actuating mechanism is engaged. The laterally varying eccentric configuration of inner surface 307 and outer surface 305 causes the flexible distal end tube to convert to a thrombus engaging configuration once tension is applied. For example, the flexible distal end tube may be more likely to bend inward in the direction of regions of eccentricity where the inner surface 307 is relatively near the outer surface 305. By varying the eccentricity laterally, the flexible distal end tube may comprise a highly irregular configuration once the actuating mechanism is engaged. In addition, interstices may be created on the surface of the flexible distal end tube, which may assist in its ability to engage a thrombus for removal from the patient's body.

Figure 4A:
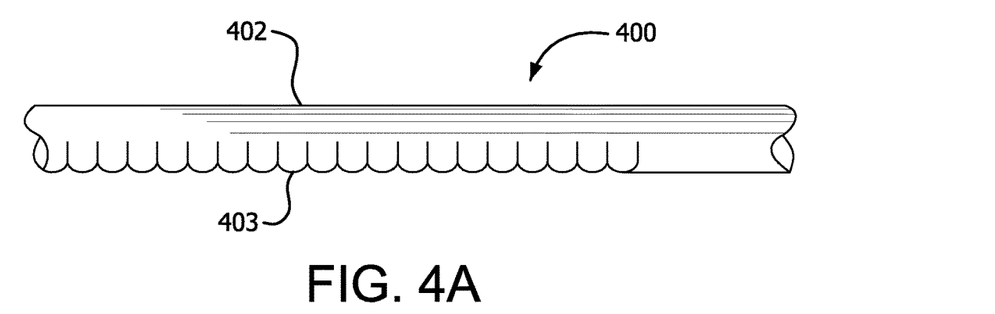
FIGS. 4A, 4B and 4C illustrate, respectively, a side view of a segment of an exemplary catheter and transverse cross-sectional views of two exemplary catheters.

With reference to FIG. 4A, a side view of an exemplary catheter 400 is illustrated. Catheter 400 includes an inner mandrel (not shown), an actuating mechanism (not shown), a flexible distal end tube 402 and corrugations 403. In various exemplary embodiments, corrugations 403 are irregularly spaced and shaped to create a pseudo-random pattern. In various exemplary embodiments, 100% or less than 100% of the surface of flexible distal end tube 402 is corrugated. In preferred embodiments, about 50% or less of the surface of flexible distal end tube 402 is corrugated. As the inner mandrel is withdrawn, tension is provided to the actuating mechanism. The tension causes flexible distal end tube 402 to take on a thrombus engaging configuration based on the position of corrugations 403.

Figure 4B:
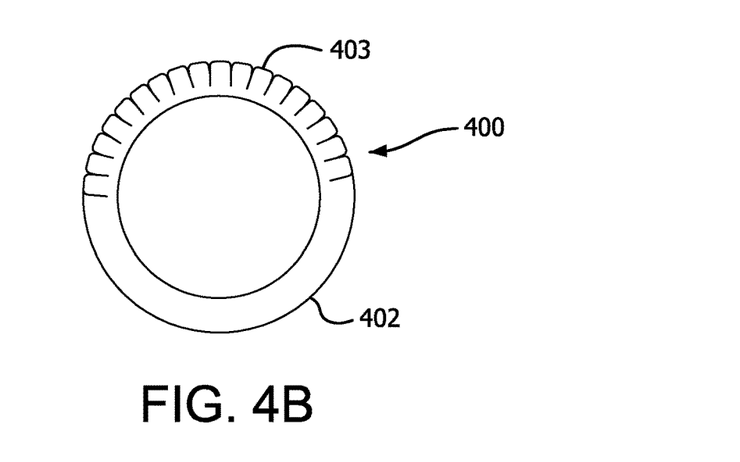
Figure 4C:
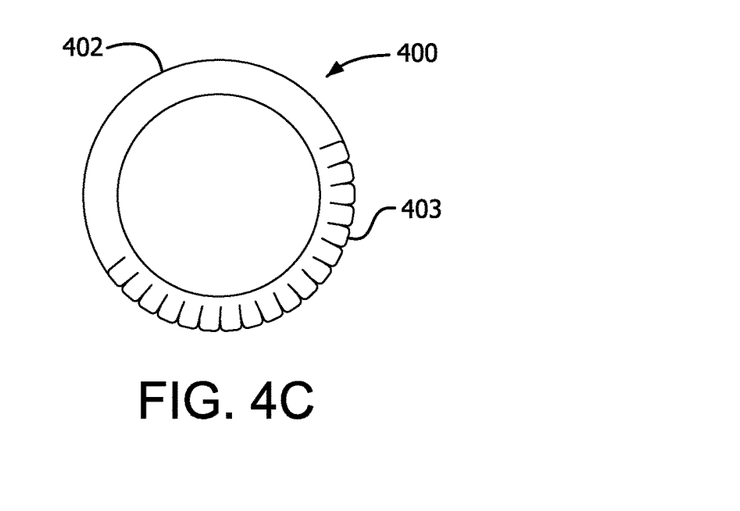

Corrugations 403 may vary laterally across flexible distal end tube 402. For example, FIGS. 4B and 4C illustrate an embodiment in which less than 100% of the circumferential surface of flexible distal end tube 402 is corrugated. In exemplary embodiments using this configuration, at different points across the lateral length of flexible distal end tube, corrugations 403 may be configured differently. FIG. 4B illustrates a cross section of flexible distal end tube 402 in which corrugations 403 comprise about 50% or less of the surface area. FIG. 4C illustrates another cross section of the same flexible distal end tube 402 at a different lateral position. Any degree of corrugation that produces a thrombus engaging configuration of flexible distal end tube 402 is within the scope of the present disclosure.

The surface of flexible distal end tube 402 may be sintered, laser treated or subjected to any other treatment which creates corrugations on the tube's surface. In addition to corrugation, the surface of flexible distal end tube 402 may be subjected to other treatments to improve the tube's ability to engage and retain a thrombus. The surface of flexible distal end tube 402 may also be impregnated with or otherwise made to incorporate materials which improve the tube's ability to engage and retain a thrombus. Any such treatment is within the scope of the present disclosure.

Figure 5A:
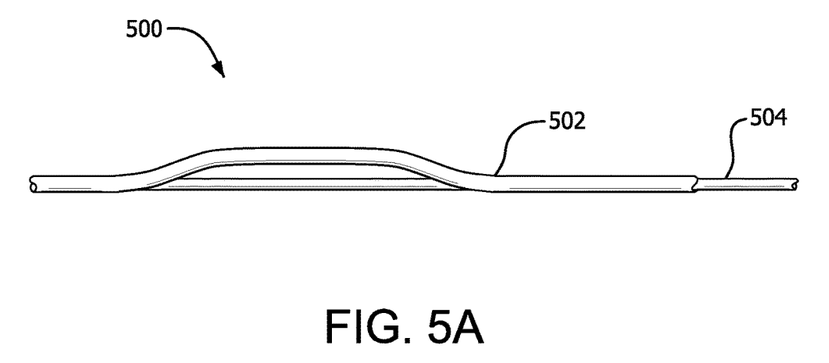
FIGS. 5A and 5B illustrate sequential side views of an exemplary catheter.
Figure 5B:
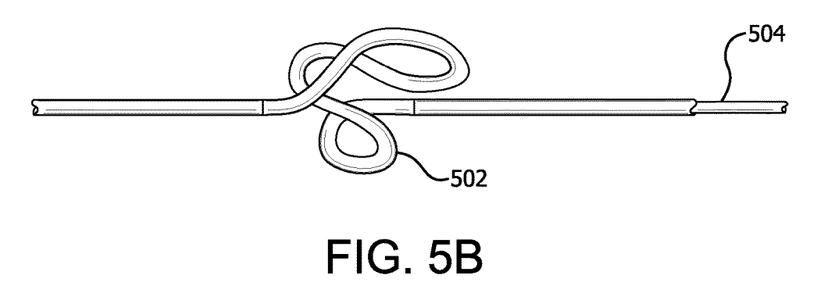

With reference to FIG. 5, a side view of an exemplary catheter 500 is illustrated. Catheter 500 comprises an inner mandrel 504, a flexible distal end tube 502, a distal tip, and an actuating mechanism. In various exemplary embodiments, inner mandrel 504 provides internal support for a portion of flexible distal end tube 502. In these embodiments, at least a portion of flexible distal end tube 502 is configured outside of inner mandrel 504. The distal tip may be situated at the distal end of inner mandrel 504.

In various exemplary embodiments, the actuating mechanism is a tension filament and is connected to the distal end of flexible distal end tube 502. In the substantially straight configuration, no tension is applied to the actuating mechanism. When tension is applied to the actuating mechanism, the portion of flexible distal end tube that is not internally supported by inner mandrel 504 may coil irregularly. As discussed in other exemplary embodiments, flexible distal end tube 502 may include corrugations, an eccentric inner and outer surface, or any other configuration that facilitates irregular coiling of the tube.

Figure 6A:
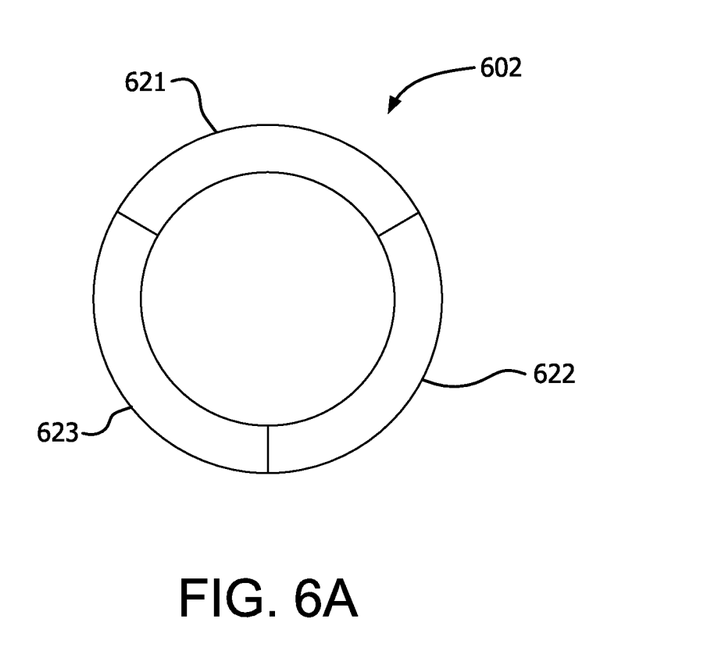
FIGS. 6A and 6B illustrate transverse cross-sectional views of an exemplary catheter.
Figure 6B:
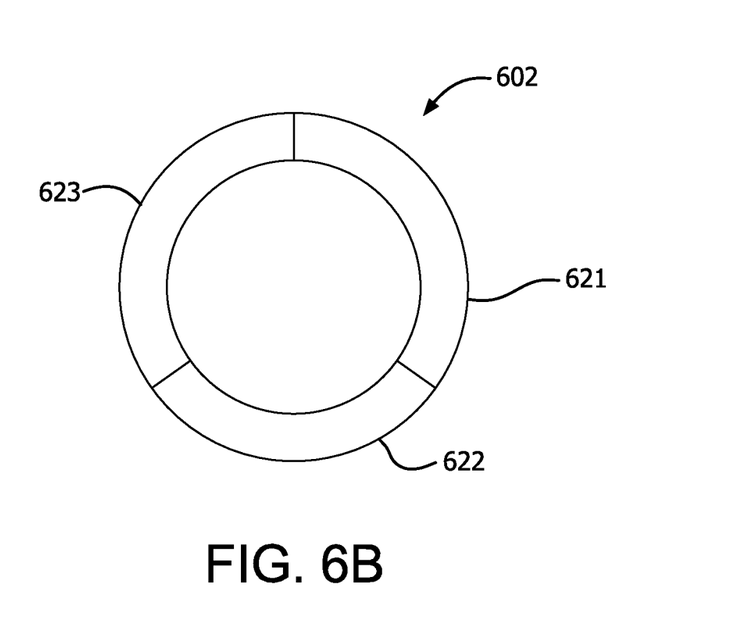

In still another exemplary embodiment, and with reference to FIGS. 6A and 6B, cross sections of an exemplary flexible distal end tube 602 are illustrated. In various exemplary embodiments, flexible distal end tube 602 may comprise a number of segments of differing flexibility (e.g., having differing durometer or hardness). In exemplary embodiments, segments of differing flexibility may be useful in biasing random actuation of the flexible distal end tube. In the illustrated exemplary embodiment, flexible distal end tube 602 comprises a relatively high flexibility segment 621, a relatively moderate flexibility segment 622, and a relatively low flexibility segment 623. However, any number of segments of differing flexibility is within the scope of the present disclosure.

In various exemplary embodiments, the positions of the segments of differing flexibility may vary laterally along flexible distal end tube 602. In various exemplary embodiments, a profile (e.g., cross-sectional view) of flexible distal end tube 602 taken at a particular lateral point may comprise an arrangement of segments 621, 622 and 623 which is different from a profile taken at a different lateral point in the tube. For example, FIG. 6A illustrates an exemplary arrangement of segments 621, 622 and 623 at a particular lateral point on flexible distal end tube 602. FIG. 6B illustrates the same exemplary flexible end tube 602 at a different lateral point along the tube. The laterally varying arrangement of segments of differing flexibility cause the flexible distal end tube 602 to convert to an irregularly coiled configuration when tension is applied by actuating mechanism. In addition, interstices may be created on the surface of flexible distal end tube 602 as it is converted to the thrombus engaging position, which may assist in its ability to engage a thrombus for removal from the patient's body.

In various exemplary embodiments, catheter 100 is withdrawn to a larger, anchored catheter. The larger, anchored catheter may comprise a balloon anchored catheter. It is typically situated well proximal to the vicinity of thrombus 112, far enough away to allow catheter 100 to be deployed and navigated to thrombus 112 effectively. In various exemplary embodiments, catheter 100 is withdrawn to the larger, anchored catheter, and thrombus 112 is aspirated within the larger catheter.

In an exemplary embodiment, thrombus 112 may be too large to remove in a single application of catheter 100. Therefore, it may be necessary to reintroduce catheter 100 to the vicinity of thrombus 112 after a portion of thrombus 112 is removed to retrieve the remaining segment of thrombus 112. In addition, in various exemplary embodiments, catheter 100 may be used to remove multiple thrombi 112 from either the same or multiple vessels. In various exemplary embodiments, catheter 100 does not need to be removed from the patient's body before reintroduction of the flexible distal end tube 102 to the vicinity of thrombus 112. For example, using the above described larger, anchored catheter, multiple introductions may be made by the flexible distal end tube 102 to the vicinity of thrombus 112 without removing catheter 100 from the patient's body. The use of a single introduction of catheter 100, as well as any number of multiple introductions, is in accordance with the present invention.

A major drawback of currently available clot removal devices is the fact that they must be fully withdrawn from the patient after the thrombus has been retrieved. This significantly lengthens procedural time and radiation exposure.

Figure 7A:
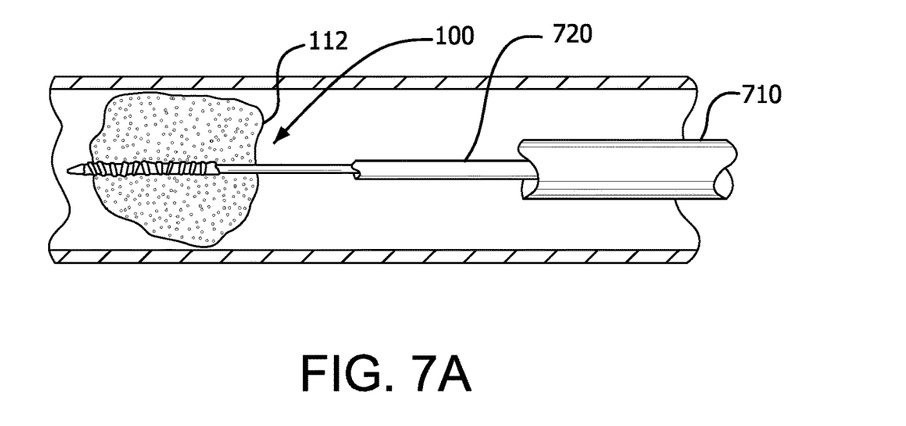
FIGS. 7A-7F show sequential side views of an aspiration catheter fitted coaxially about the exemplary catheter and used to pierce and collect thrombus.
Figure 7B:
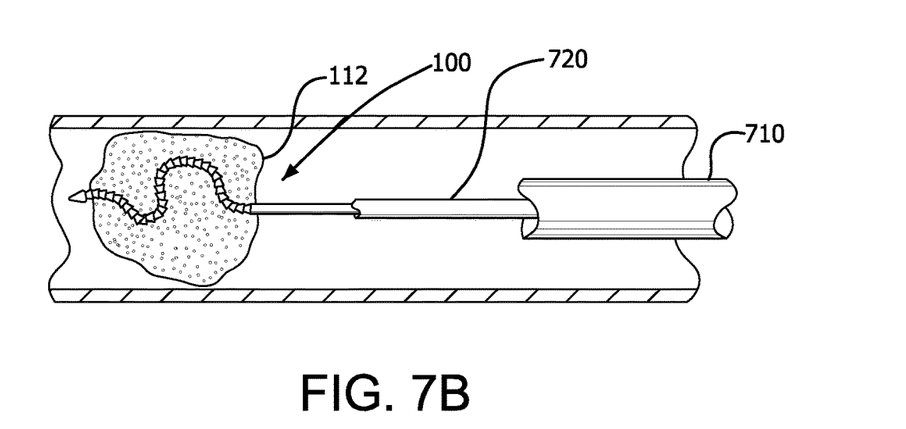
Figure 7C:
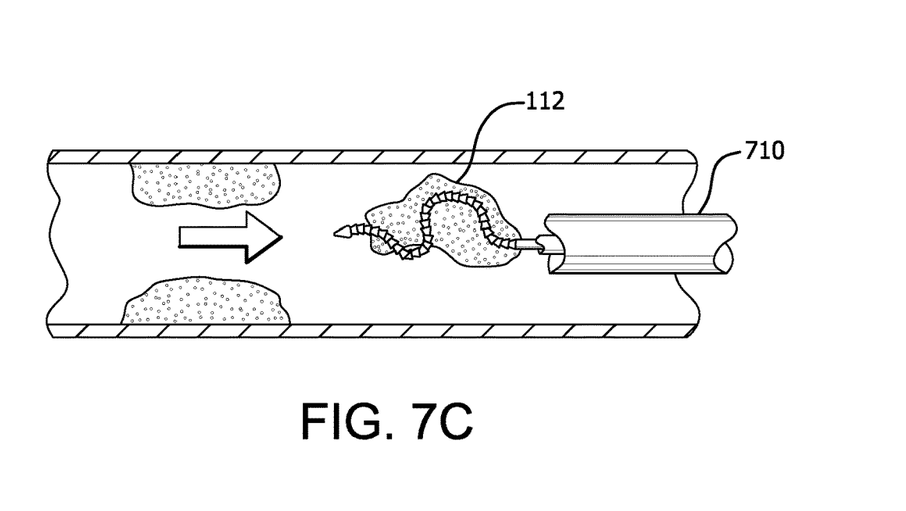
Figure 7D:
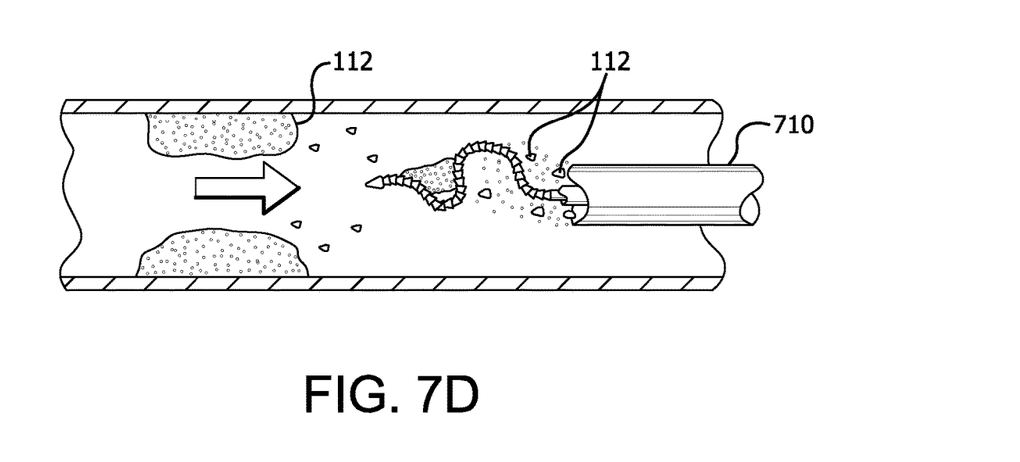
Figure 7E:
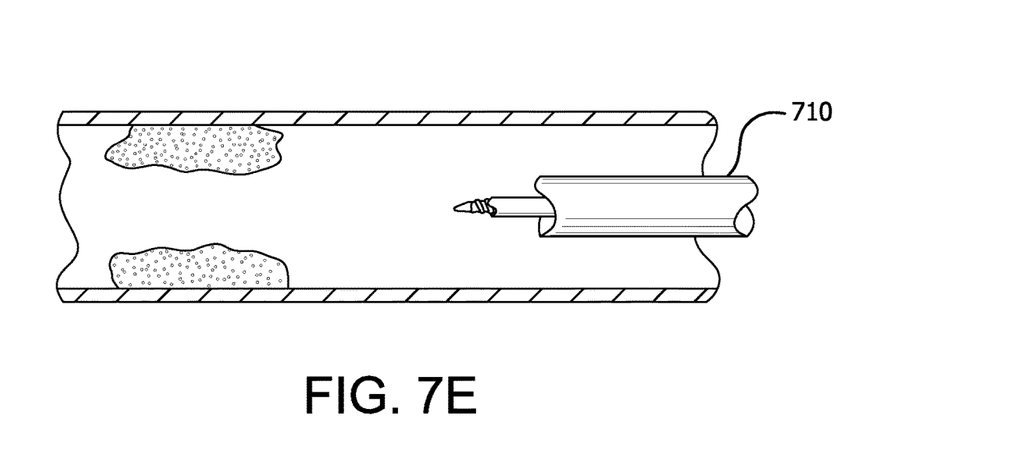
Figure 7F:
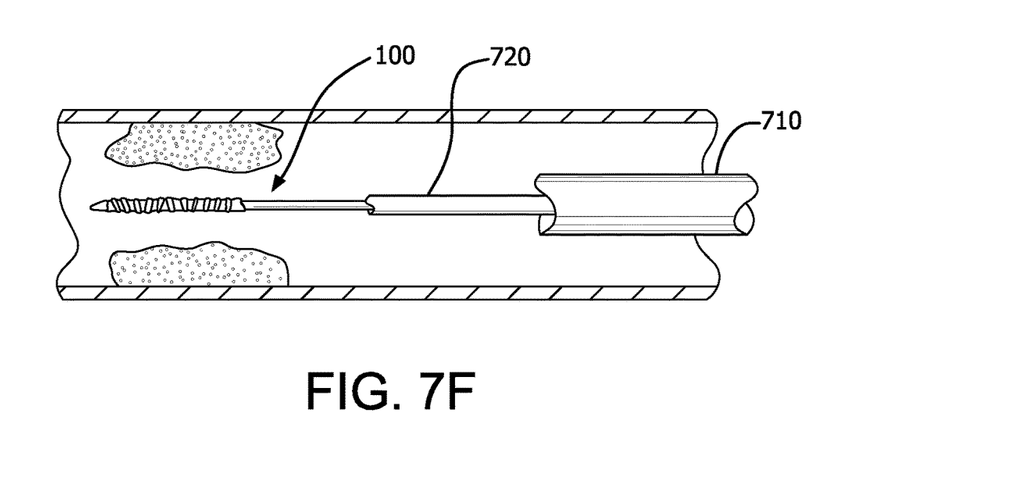

The present invention overcomes this limitation by utilizing an aspiration catheter 710 concentrically located to microcatheter 720 as shown in FIG. 7A. The catheter 100 is advanced into the thrombus 112 burden and actuated (as in FIG. 7B) to acquire/grasp the thrombus 112. Tension is applied to the catheter 100, thus dislodging thrombus 112 (or a portion thereof). The thrombus 112 burden is drawn back to the mouth of the aspiration catheter 710 as shown in FIG. 7C. Drawing negative pressure (as with a syringe) on the aspiration catheter 710 will pull the thrombus 112 from the catheter 100 and into the aspiration catheter 710 lumen. This effect is depicted in FIG. 7D. During aspiration, the catheter 100 may be withdrawn into the microcatheter 720 as in FIG. 7E. Withdrawing the catheter 100 will re-configure it to a condition suitable for re-entry further into the host vessel and remaining indwelling thrombus. This procedure of gasping, sweeping and re-grasping may be repeated without need to remove the system from the patient.

Figure 8A:
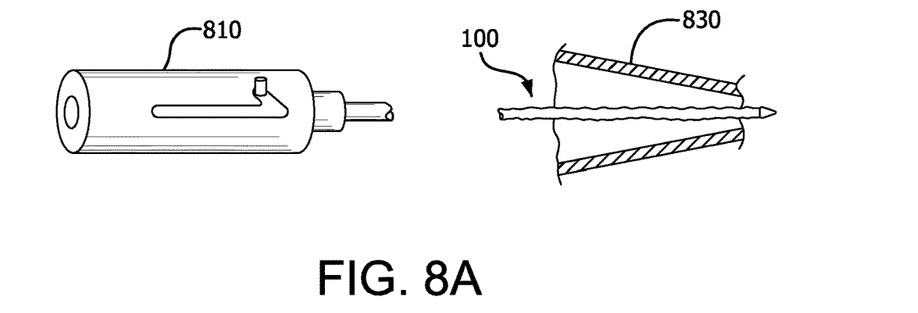
FIGS. 8A-8C show the use of a handle with the device.
Figure 8B:
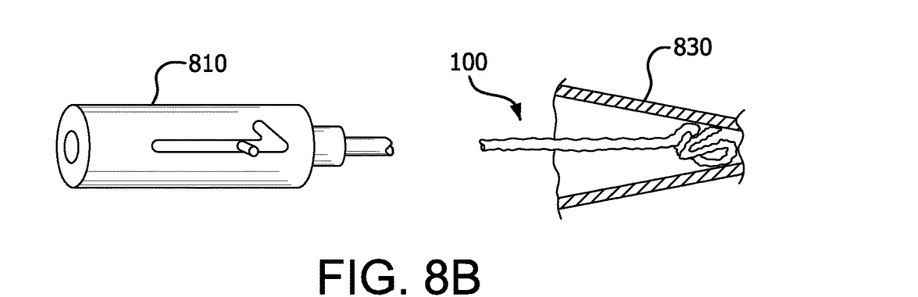
Figure 8C:
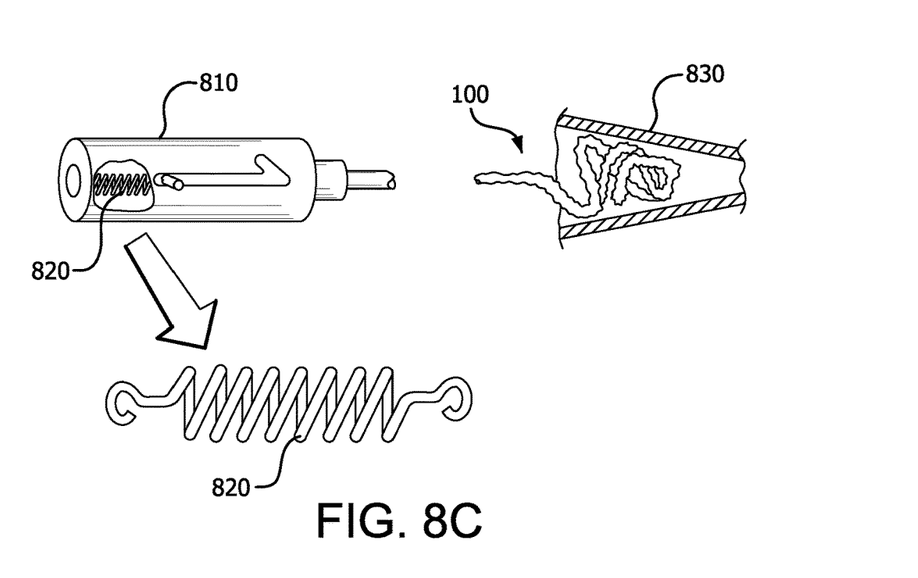
Figure 9A:
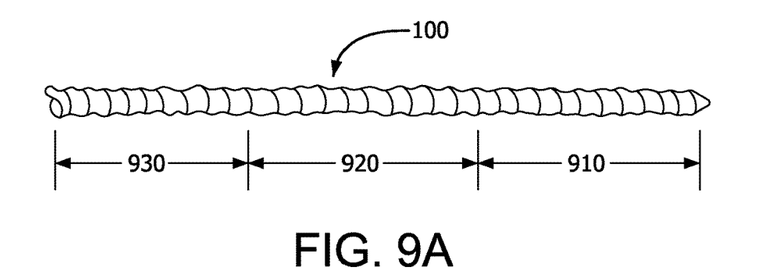
FIGS. 9A-9D show how the device may be configured to actuate in sequential zones.
Figure 9B:
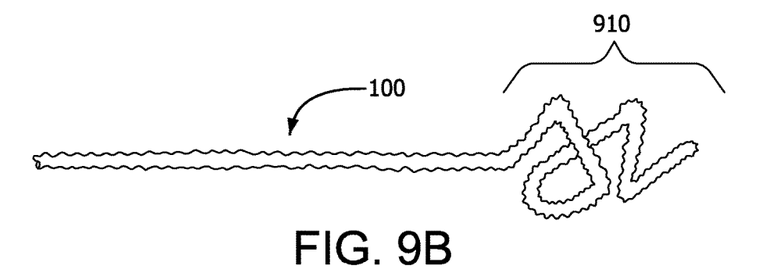
Figure 9C:
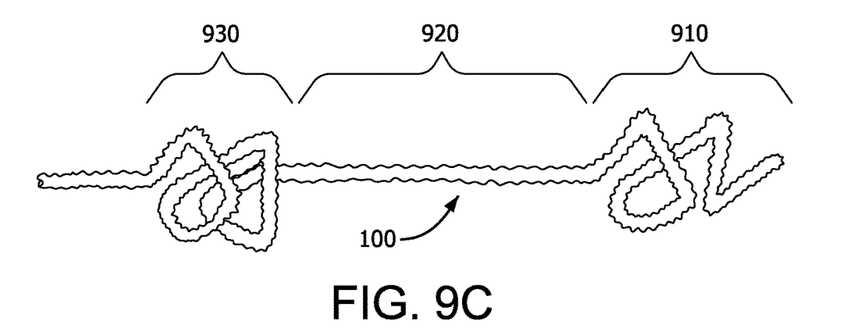
Figure 9D:
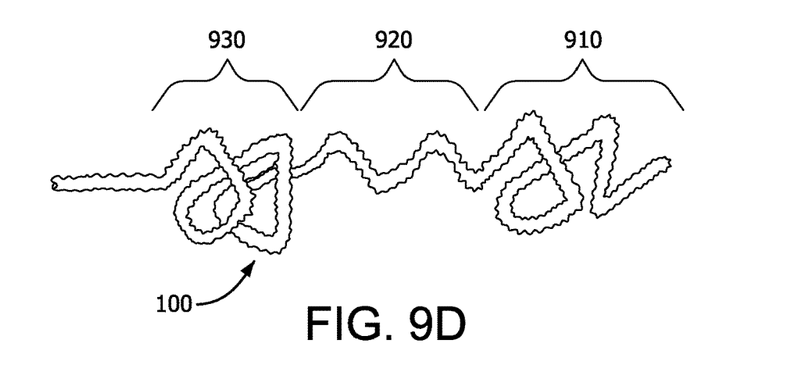

It is envisioned that various handle embodiments may be included, which enhance performance of the device as generally shown in FIGS. 8A-8C. For instance, a handle 810 located near the operator could be configured to apply a constant tension to the device 100. This constant tension (such as through the use of a spring 820) would allow the device 100 to constantly change its shape as it is moved within the vessel 830.

As well, the recanalization device 100 may be configured to actuate in sequential zones as generally shown in FIGS. 9A-9D, i.e. applying tension may first cause the most distal portion 910 to actuate into a random configuration. Applying further tension may cause the most proximal portion 930 to actuate. With distal and proximal sections actuated, thrombus is trapped. Further tension may now cause middle section 920 to actuate. The device 100 is now capable of withdrawing thrombus from the host vessel with little chance of releasing emboli.

It is apparent that the recanalization device described herein provides an effective, low crossing catheter capable of removing thrombi from delicate vasculature, including neurovasculature.

EXAMPLE 1

A 0.35 mm diameter stainless steel wire was obtained. This wire served as a mandrel upon which was wrapped in a bias-ply helical fashion a length of tape that had been slit from an ePTFE film, the film made as described in U.S. Pat. No. 5,476,589 to Bacino. To create the tape, the thin ePTFE film was slit to approx 3 mm wide and helically wrapped upon the wire mandrel with minimal tension until the layer built up a wall thickness of approx 0.1 mm. An approx 15 cm long section was fabricated in this way and then subjected to a thermal treatment for 10 minutes in a Grieves Model 1100 convection air oven thermostatically set to operate at 370° C.

Upon removal from the oven and cooling, approximately ½ of the length of the ePTFE tube was axially compressed. This compression cased wrinkling to occur in the compressed section. This wrinkling was not necessarily uniform. The ends of the tube were temporarily secured to the mandrel by tightly wrapping each end with a fine silver plated copper (SPC) wire over-wrap and then subjected to another thermal treatment in the same oven at the same temperature for 15 minutes. This treatment semi-densifies the wrinkles in place.

Upon removal from the oven and cooling, the ePTFE tube was removed from the mandrel and a smaller stainless steel wire of about 0.15 mm diameter was inserted through the corrugated tube until the end of the wire reached the end of the tube. The end of this wire was affixed to the tip of the corrugated tube with Loctite® adhesive.

To activate the device, tension is applied to the 0.15 mm diameter wire which causes the corrugated section of the ePTFE tube to take on an irregular shape. This irregular shape, along with the extra surface area provided by the corrugated surface, provided the required clot retention properties to facilitate clot/debris/emboli removal from the host vessel.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

We claim:

1. A catheter comprising:
a tip;
a monolithic distal end tube is polymeric and flexible and which comprises a substantially linear state and an irregularly coiled state, the monolithic distal end tube having an inner lumen extending within the monolithic distal end tube, the monolithic distal end tube including an outer surface and an inner surface defining the inner lumen of the monolithic distal end tube, the inner surface being eccentric to the outer surface at a plurality of locations along the longitudinal length of the monolithic distal end tube such that an arrangement of the inner surface and the outer surface of the monolithic distal end tube varies along the monolithic distal end tube and a cross-section of the monolithic distal end tube taken at a first of the plurality of locations comprises an arrangement of the inner surface and the outer surface that is different from a cross-section taken at a second of the plurality of locations; and
an inner mandrel removably received in the inner lumen of the monolithic distal end tube, the inner mandrel providing column strength to the monolithic distal end tube to support the monolithic distal end tube in a substantially linear configuration.

2. The catheter of claim 1, further comprising:
a line;
wherein the monolithic distal end tube is transitionable between the substantially linear state and the irregularly coiled state, wherein an application of tension to the line causes the monolithic distal end tube to adopt the irregularly coiled state, and wherein a release of tension to the line causes the monolithic distal end tube to adopt the substantially linear state.

3. The catheter of claim 2, wherein the monolithic distal end tube comprises a plurality of segments of different flexibility.

4. The catheter of claim 2, wherein the line is attached to at least a portion of the monolithic distal end tube.

5. The catheter of claim 4, wherein the line is a wire.

6. The catheter of claim 4, wherein the line is a filament.

7. The catheter of claim 1, wherein the monolithic distal end tube comprises a corrugated polymer.

8. The catheter of claim 7, wherein the monolithic distal end tube is corrugated in an irregular manner.

9. The catheter of claim 8, wherein the corrugation is asymmetrical across a diametric axis of the monolithic distal end tube.

10. The catheter of claim 7, wherein less than 100% of the outer surface of the monolithic distal end tube is corrugated.

11. The catheter of claim 7, wherein the monolithic distal end tube comprises one from the group of ePTFE, nylon, polycarbonate, polyethylene, polypropylene, polyvinyl chloride, polyurethane, and polysiloxane.

12. The catheter of claim 11, wherein the polymer is semi-porous.

13. The catheter of claim 1, wherein the position of the inner surface in relation to the outer surface varies axially along the length of the monolithic distal end tube.

14. The catheter of claim 1, wherein a portion of the monolithic distal end tube is outside of the inner mandrel.

15. The catheter of claim 1, further comprising a radiopaque material.

16. The catheter of claim 1, wherein the tip comprises a radiopaque material.

17. The catheter of claim 1, wherein the tip comprises a densified end segment of the monolithic distal end tube.

18. The catheter of claim 1, further comprising an actuating mechanism configured to apply vacuum to the monolithic distal end tube.

19. The catheter of claim 1, wherein the tip is a thrombus piercing tip; and wherein the monolithic distal end tube is formed entirely of semi-porous ePTFE including a plurality of semi-densified wrinkles defining a series of irregular corrugations in the semi-porous ePTFE of the monolithic distal end tube.

* * * * *